United States Patent
Keranen

(10) Patent No.: US 12,329,854 B2
(45) Date of Patent: Jun. 17, 2025

(54) FLAVORED BIOACTIVE EXTRACTS AND METHODS OF FLAVOR INTRODUCTION

(71) Applicant: Pure Laboratories, LLC, Gainesville, FL (US)

(72) Inventor: Mark D. Keranen, Tampa, FL (US)

(73) Assignee: Pure Laboratories, LLC, Gainesville, FL (US)

( * ) Notice: Subject to any disclaimer, the term of this patent is extended or adjusted under 35 U.S.C. 154(b) by 527 days.

(21) Appl. No.: 17/063,516

(22) Filed: Oct. 5, 2020

(65) Prior Publication Data

US 2021/0100741 A1 Apr. 8, 2021

Related U.S. Application Data

(60) Provisional application No. 62/910,717, filed on Oct. 4, 2019.

(51) Int. Cl.

| | |
|---|---|
| *A23L 27/28* | (2016.01) |
| *A23L 27/10* | (2016.01) |
| *A61K 9/00* | (2006.01) |
| *A61K 31/047* | (2006.01) |
| *A61K 31/352* | (2006.01) |
| *A61K 31/366* | (2006.01) |
| *A61K 36/185* | (2006.01) |
| *A61K 47/10* | (2017.01) |
| *A61K 47/46* | (2006.01) |

(52) U.S. Cl.
CPC ............ *A61K 9/0056* (2013.01); *A23L 27/10* (2016.08); *A23L 27/28* (2016.08); *A61K 9/007* (2013.01); *A61K 31/047* (2013.01); *A61K 31/352* (2013.01); *A61K 31/366* (2013.01); *A61K 36/185* (2013.01); *A61K 47/10* (2013.01); *A61K 47/46* (2013.01); *A23V 2002/00* (2013.01)

(58) Field of Classification Search
CPC .... A61K 9/0056; A61K 9/007; A61K 31/047; A61K 31/352; A61K 31/366; A61K 36/185; A61K 47/10; A61K 47/46; A23L 27/28; A23L 27/10
USPC ......................................................... 514/455
See application file for complete search history.

(56) References Cited

U.S. PATENT DOCUMENTS

| | | |
|---|---|---|
| 10,624,940 B2 | 4/2020 | Speier |
| 2017/0095624 A1 | 4/2017 | Davidson et al. |
| 2018/0296493 A1 | 10/2018 | Kaufman |
| 2019/0209633 A1 | 7/2019 | Speier |
| 2021/0059307 A1 | 3/2021 | Engqvist |

FOREIGN PATENT DOCUMENTS

| | | |
|---|---|---|
| WO | 2013011899 | 1/2013 |
| WO | 2019048880 | 3/2019 |

OTHER PUBLICATIONS

Kava; Wikipedia article dated Sep. 24, 2019 (Sep. 24, 2019) accessed at httpszllenwikipedia.org/wiindex.php?title=Kava&oldid=917588284.

Zhang et al., "Electrospun Nancfibres Containing Antimicrobial Plant Extracts" Nanomaterials vol. 7, No. 42, pp. 1-17; Feb. 15, 2017 (Feb. 15, 2017) Abstract; entire document.

PCT Search Report, PCT Application No. PCT/US2020/054306, Feb. 9, 2021.

Office Action issued Sep. 19, 2024 in connection with corresponding Canadian Patent Application No. 3,153,511.

Office Action issued Jul. 25,. 2023 in connection with corresponding Canadian Patent Application No. 3,153,511.

*Primary Examiner* — Yevgeny Valenrod

(74) *Attorney, Agent, or Firm* — Akerman LLP; Peter A. Chiabotti; Ryan Harding

(57) ABSTRACT

A flavored bioactive extract may include a homogeneous flavored bioactive extract composition including a bioactive plant extract, flavoring, and a carrier. The carrier may be hydrophilic and the extract may have a crystalized or resinous form. The flavoring may be non-lipophilic or hydrophilic.

27 Claims, No Drawings

FLAVORED BIOACTIVE EXTRACTS AND METHODS OF FLAVOR INTRODUCTION

CROSS-REFERENCE TO RELATED APPLICATIONS

The present application claims priority to U.S. Provisional Application 62/910,717, filed Oct. 4, 2019, titled Method of Flavor Introduction, the contents of which are hereby incorporated herein by reference.

TECHNICAL FIELD

A method for introduction of flavors into bioactive extracts of plants such as *Cannabis sativa,* obtained from any part of the plant such as glandular trichomes, stems/stalks, leaves, flowers and roots, is described.

BACKGROUND

Plant material may be subjected to extraction to separate various plant components for commercial and industrial applications. Extraction may include grinding plant material and thereafter extracting and further isolating or purifying extracted plant compounds using various techniques that may include utilization of solvents, pressure, microwave, supercritical fluid, ultrasound, heating, cooling, evaporation, condensation, distillation, among others. Bioactive compounds obtained from such extraction techniques have a number of beneficial uses in the medicinal, cosmetic, and food arts.

SUMMARY

In one aspect, a flavored bioactive extract includes a homogeneous flavored bioactive extract composition including a bioactive plant extract, flavoring, and a carrier. The carrier may be hydrophilic and the extract may have a crystalized or resinous form. In one example, the flavoring may be non-lipophilic or hydrophilic.

In yet another aspect, a method of flavoring a bioactive extract includes applying heat to a bioactive plant extract, and heating the extract to a sufficient temperature to melt or soften the extract to obtain a workable extract melt. The method also includes adding flavoring to the extract melt and mixing until complete dissolution of the flavoring within the extract and subsequently allowing the homogenous product to cool. In one example, the flavoring is added while heat is being applied to the extract melt. In another embodiment, the flavoring is added after the extract melt has been removed from heat. In one example, the flavoring is added to the extract within a carrier solution such as vegetable glycerin (VC), propylene glycol (PG), or combination thereof. In one example, the flavoring and carrier mixture is mixed with the extract while heat is being applied. In another embodiment, the carrier mixture is mixed with the extract following removal of the extract from applied heat.

In another aspect, a method of formulating uniformly infused flavored crumble includes combining a bioactive plant extract, flavor, and carrier and homogenizing the mixture to achieve complete dissolution of the ingredients. Water, such as distilled water, may then be added and the mixture further stirred to introduce the water. The mixture may then be allowed to recrystallize for flavor infusion to take place. Recrystallization typically takes place in about an hour at around room temperature for a mixture under 1 L. The resulting slurry may be subjected to one or more rounds of vacuum filtration and washing with distilled water and allowed to dry.

In still another aspect, a method of formulating uniformly infused flavored crumble includes combining a bioactive plant extract, flavor, and carrier and homogenizing the mixture to achieve complete dissolution of the ingredients. The mixture is then sealed within a vessel and allowed to recrystallize for about 24 hours or longer. The mixture is preferably undisturbed during the recrystallization period. Thereafter, water, such as distilled water, may be added and briefly stirred. The resulting suspension of crystals may be separated from the bulk solution by vacuum filtrated to yields a crude flavored product. The crystals may then be washed with water, typically at about room temperature or colder, to remove excess carrier solvent. The product may then be dried. For example, the product may be spread along a surface to air dry at about room temperature.

In yet another aspect, a method of formulating a homogeneous flavored bioactive plant product having a crystalized or resinous form comprises applying heat to a bioactive plant extract until the extract is melted or softened to a workable consistency to form a melt; combining a flavoring and hydrophilic carrier with the melt until dissolution of the flavoring and carrier in the melt; and cooling the mixture of flavoring, carrier, and extract, wherein at room temperature the homogenous flavored bioactive plant product is crystalized or resinous.

In one example, the flavoring is non-lipophilic or hydrophilic.

In the above or another example, the heat is applied between about 75° C. and about 100° C., within about 30° C. of the melting point of the extract, or within about 10° C. of the melting point of the extract.

In any of the above or another example, the extract may include a crystalline/resinous lipophilic plant extract.

In any of the above or another example, the extract comprises or consists of (a) cannabinoid or cannabinoid acidic precursor isolates; (b) one or more of cannabidiol (CBD), CBDa, cannabigerol (CBG), cannabinol (CBN), tetrahydrocannabinol (THC) Δ8 or Δ9, THCa, cannabichromene (CBC), or cannabidivarin (CBDV); (c) one or more of kavalactones, kratom (mitragynine and 7-hydroxymitragynine), and combinations thereof; (d) flavonoids and alkaloid/protoalkaloid/pseudoalkaloid; (e) caffeine, psylocin/psilocybin and mitragynine, 7-OH-mitragynine, yohimbine, voacangine, or related compounds.

In any of the above or another example, the carrier comprises a GRAS for inhalation carrier.

In any of the above or another example, the carrier comprises or consists of VG, PG, or combination thereof.

In any of the above or another example, the flavoring comprises menthol or coffee flavoring. In any of the above or another example, the flavoring and carrier are combined in an amount about 30% or less of the homogenous flavored bioactive plant product.

In any of the above or another example, the extract comprises a kavalactone extract and the heat is applied at a temperature between about 140° C. and 160° C.

In any of the above or another example, the extract comprises one or more of cannabidiol (CBD), CBDa, cannabigerol (CBG), cannabinol (CBN), tetrahydrocannabinol (THC) Δ8 or Δ9, THCa, cannabichromene (CBC), or cannabidivarin (CBDV), and the heat is applied at a temperature between about 60° C. and 95° C.

In any of the above or another example, wherein the heat is applied at a temperature between about 80° C. and 95° C.

In still another aspect, a method of formulating a homogeneous flavored bioactive crumble product may include combining a bioactive plant extract, hydrophilic or non-lipophilic flavoring, and hydrophilic carrier and homogenizing the resultant mixture until dissolution of the flavoring and carrier within the extract; adding an aqueous solution to the mixture and stirring to introduce the solution; allowing the mixture with the introduced solution to crystallize; and subjecting the crystallized mixture to one or more rounds of vacuum filtration.

In still yet another aspect, a method of formulating a homogeneous flavored bioactive crumble product includes combining a bioactive plant extract, non-lipophilic or hydrophilic flavoring, and hydrophilic carrier and homogenizing the resultant mixture until dissolution of the flavoring and carrier within the extract; adding an aqueous solution to the mixture and stirring to introduce the solution; sealing the mixture with the introduced solution in a container for about 24 hours or longer to crystallize; suspending the crystals in aqueous solution and subjected the crystallized mixture to one or more rounds of vacuum filtration to yield a crude flavored product; washing the crude flavored product with aqueous or other suitable solution to remove excess carrier; and drying the washed product on a surface at about room temperature.

DETAILED DESCRIPTION

The present disclosure describes homogeneous flavored bioactive plant extracts and methods of introducing flavors into bioactive plant extracts to formulate flavored products. The flavored bioactive extract products may be formulated to comprise a homogeneous composition including a bioactive plant extract, flavoring, and a carrier.

In various embodiments, a method of flavoring a bioactive extract includes applying heat to a solid bioactive plant extract, such as a resin, heating the resin to a sufficient temperature to melt or soften the resin extract, and mixing flavoring with the melted or softened extract until dissolution within the melt. The mixture may be cooled wherein after cooling the flavoring does not separate from the resin and provides a consistent flavor profile.

The methodology may utilize low heat to promote slow melting or softening/liquification of the plant resin before flavoring contained in a carrier comprising or consisting of vegetable glycerin (VG), propylene glycol (PG), a mixture of VG and PG, or other suitable non-lipophilic or hydrophilic flavor carrier, is introduced. In various embodiments, an appropriate amount of flavoring will vary from formulation to formulation but will typically range from 3% to 20% by weight of the finished product. The combined resin and flavoring are mixed and then allowed to cool, creating a flavored concentrate that can be consumed via existing methods of concentrate use—primarily inhalation, e.g., in combination with devices for dabs, shatter, budder, resin, waxes and related forms such as nails, e-nails, nectar collectors and related devices. The resulting flavored product may recrystallize completely or may exist as a resinous form. It is to be appreciated that lipophilic flavorings may be utilized in addition to non-lipophilic or hydrophilic flavorings, the former being accomplished via known methods prior to, during, or after addition of non-lipophilic or hydrophilic flavoring described herein.

The bioactive plant extracts utilized may be solid or semi-solid extracts at room temperature. For example, the plant extracts may comprise crystalline/resinous lipophilic extracts including isolates, distillates, refined distillates, or the like. For brevity, the bioactive plant extracts may be generally referred resins or extracts herein. The bioactive plant extracts may be obtained in any manner from any part of the plant such as glandular trichomes, stems/stalks, leaves, flowers and/or roots.

Example extracts for flavor introduction include isolates and distillates including crude, refined, purified, and combinational extracts of various spectrums (e.g., partial, full, broad) and purities. In some embodiments, the extracts used for flavor introduction may include cannabinoids and the acidic precursors when applicable. The extracts may include those of the *Cannabis* genus, for example. Presently preferred extracts include cannabinoid isolates including one or more of cannabidiol (CBD), CBDa, cannabigerol (CBG), cannabinol (CBN), tetrahydrocannabinol (THC) $\Delta 8$ or $\Delta 9$, THCa, cannabichromene (CBC), cannabidivarin (CBDV), and/or other cannabinoids, kavalactones, kratom (mitragynine and 7-hydroxymitragynine, and combinations thereof. Those having skill in the art will recognize the methodologies described herein may be applied to additional bioactive plant extracts. For example, further examples of extracts for flavor introduction may include flavonoids and alkaloid/protoalkaloid/pseudoalkaloid extracts ranging from caffeine to psylocin/psilocybin and mitragynine, 7-OH-mitragynine, yohimbine, voacangine, and related compounds. These extracts usually require organic solvents and/or salting out techniques to process and introduce into products. However, the present methodologies may also be utilized to flavor any resinous extract, even those that are known to be typically difficult to work with in the absence of organic solvents or salting out techniques. The methods described herein allow for rapid introduction of flavors into such resins to prepare flavored products ready for consumption without the use of hazardous solvents or pH manipulations.

As introduced above, heat may be applied to the extract to melt or soften the resin into a workable state. It is typically desirable to heat the resin to about at or above its melting point, but below temperatures wherein the various components or the extract deteriorate, chemically react, decompose, decarboxylate, boil, or vaporize. Thus, temperature required to generate a workable resin, or extract, melt, in certain combinational extracts, such as full or broad-spectrum extracts, may be determined by the combination of components and the bulk melting temperature of the extract. The workable resin will typically be at a temperature between about 70° C. and about 90° C., depending on the particular extract selected and composition when heating is complete. For example, workable melted CBD isolate at 83° C. is fully melted, has a viscosity measured around 130 cps, and is clear with a light yellow color.

Further to the above, the extent of heating will typically be dependent on the melting point of the extract being infused with flavor. In the processing of cannabinoid and other isolates, for example, isolates of CBD extracts have an associated melting point of about 66° C., CBG extracts have an associated melting point around 52° C., CBN extracts have a melting point around 77° C., and THC $\Delta 9$ extracts have a melting point around 62° C. Melting points of other extract compositions are known or easily measured by those skilled in the art. For full and broad-spectrum distillates, which vary in composition and purity, a similar strategy may be applied. For example, in these cases, heating may be applied to about or just above the bulk melting point, which is usually about 60° C. to about 80° C., for flavor introduction according the methodologies described herein. This strategy also allows one to preserve the composition of acidic cannabinoids (CBDa, THCa, etc.), if present, while avoiding decarboxylation, which occurs more rapidly at or above about 105° C.

Typically, the resin may be subjected to applied heat at a temperature at or above the melting point of the resin. In various embodiments, heat is applied at about 90° C. For example, heat may be applied at between 60° C. and about 100° C., about 60° C. and about 95° C., about 65° C. and about 90° C., about 65° C. and about 85° C., about 65° C. and about 80° C., about 70° C. and about 100° C., about 70° C. and about 95° C., about 70° C. and about 80° C., about 75° C. and about 100° C., about 75° C. and about 95° C., about 75° C. and about 90° C., about 75° C. and about 85° C., about 75° C. and about 80° C., about 80° C. and about 100° C., about 80° C. and about 95° C., about 80° C. and about 90° C., about 80° C. and about 90° C., about 80° C. and about 85° C., about 85° C. and about 100° C., about 85° C. and about 95° C., about 85° C. and about 90° C., about 90° C. and about 100° C., about 90° C. and about 95° C., or about 95° C. and about 100° C. In some embodiments, higher temperature ranges may be used for extracts having higher melting points, such as between about 100° C. and about 180° C., about 100° C. and about 160° C., about 110° C. and about 170° C., about 110° C. and about 160° C., about 110° C. and about 150° C., about 130° C. and about 180° C., about 140° C. and about 160° C., or about 140° C. and about 150° C. In further examples, applied heat may be greater than about 70° C., greater than about 80° C., greater than about 90° C., or less than about 100° C., less than about 95° C., less than 90° C., less than 85° C., or less than 80° C., less than 75° C. such that the minimum applied heat is greater than about 30° C. In various embodiments, the applied heat may correspond to the melting temperature of the resin or about 5° C., about 10° C., about 20° C., about 25° C., about 30° C., about 35° C., or about 40° C. greater than the melting temperature of the resin. In some examples, heat is applied at between about 1° C. and about 40° C., about 1° C. and about 35° C., about 1° C. and about 30° C., about 1° C. and about 25° C., about 1° C. and about 20° C., about 1° C. and about 20° C., about 1° C. and about 15° C., about 1° C. and about 10° C., about 1° C. and about 5° C., about 5° C. and about 40° C., about 5° C. and about 30° C., about 5° C. and about 20° C., about 5° C. and about 10° C., about 10° C. and about 40° C., about 10° C. and about 30° C., about 10° C. and about 20° C., about 20° C. and about 40° C., about 20° C. and about 30° C., or about 30° C. and about 40° C. greater than the melting temperature of the resin. In one embodiment, the heat is applied within about 10° C., about 5° C., about 4° C., about 3° C., about 2° C., or about 1° C. of the melting temperature of the resin.

As introduced above, heating is preferably designed to slowly heat the resin to a temperature about at or above its melting temperature, but below temperatures associated with degradation, chemical, modification, boiling, or vaporization of resin component. Lower temperatures are typically preferred.

In various embodiments, the amount of heat may be consistently applied or may be varied. For example, a greater amount of heat may be applied initially followed by a reduction in heat, or a lower amount of heat may be applied followed by an increase in heat. Both the resin and flavor ingredients can be heated to the same temperature, or alternatively the flavor ingredients can remain at room temperature, or potentially cooler, and be utilized. For larger scale production it may be beneficial to hold all inputs at the same melt temperature of the resin to aid in rapid mixing and introduction of flavor to speed up the duration of the infusion process.

Various heat sources may be used. For example, heat sources such as a hot plate, heated air, or immersion in liquid baths may be used. Indeed, the present methods tolerate varied methods of heat application. Since infusion happens in a liquid state when heated, the process easily translates from batch to flow production, where the ingredients are allowed to combine at elevated temperatures as they pass through the reactor before being collected and allowed to crystallize. In one example, microwave energy may be utilized under controls to prevent decarb of extract compounds.

When the resin is melted or softened to a workable consistency to form a workable extract melt, flavor ingredients may be added to the resin. The flavor ingredients may comprise or consist of flavoring and carrier.

Any suitable flavoring may be used provided that it is compatible with the temperatures involved in the heating process. Current extracts may be flavored by retention or introduction of terpenes and natural oils. Prior to the present invention, other flavorings, such as more complex flavorings, e.g., beverage flavorings, eFlavors (flavors utilized for e-cigarettes or vaporizers), and other various non-lipophilic or hydrophilic flavorings, could not be successfully retained within the extract and would separate from a mixture. The present methodologies, however, may be used to incorporate and/or infuse such flavorings with extracts in crystallized or resinous form and that allow the flavored products to be utilized for applications such as inhalation. The flavorings may include low melting solids such as menthol and its isomers or PG/VG solutions thereof. Flavorings may include food and beverage flavorings commonly supplied as solutions including flavoring in PG, VG, or combinations thereof. These solutions have proven to be universally applicable in the methodologies described herein as solids or liquids in pure form, irrespective of melting and boiling point. Thus, utilizing the present methods, flavorings other than hydrophobic, lipophilic, and oil-based flavorings may be utilized to flavor lipophilic extracts to formulate flavored extract products in crystalized or resinous form.

The flavoring may be added in an amount between about 1% and about 50% by weight of the product. While greater weight percentages of flavoring may be used, the amount of flavoring added decreases potency of the product and thus lower weight percentages are typically preferred. In various embodiments, flavoring is added in an amount between about 1% and about 40%, about 1% and about 20%, about 1% and about 10%, about 1% and about 5%, about 5% and about 30%, about 5% and about 25%, about 5% and about 20%, about 5% and about 15%, about 10% and about 30%, about 10% and about 25%, about 10% and about 20%, or about 10% and about 15% by weight of the flavored product. In another example, flavoring is added in an amount less than about 50%, about 40%, about 30%, about 20%, about 10%, about 5%, or about 3% by weight of the flavored product. In one embodiment, flavoring is added in an amount between about 3% and about 30% by weight of the flavored product such that the flavored product provides a potency of 70% or greater when isolates and/or refined distillates are employed.

As introduced above, flavoring will typically be added within a carrier, which will typically be a hydrophilic carrier to provide a polar environment within which the flavoring may be retained, incorporated, and/or infused within the crystalized or resinous product. Those having skill in the art will be able to identify suitable carriers upon reading the present description. Example carriers may comprise or consist of sugar alcohols, glycerol, or other GRAS solvents, such as non-lipophilic or hydrophilic flavor carriers and particularly flavor carriers GRAS for inhalation. In some formulations, the carrier comprises or consists of one or more of ethyl alcohol/ethanol, triacetin, VG, PG, or combination thereof. In one example, the carrier comprises or consists of VG, PG, or combination thereof. In various embodiments, carrier is added in an amount between about 1% and about 50%, about 1% and about 40%, about 1% and about 20%, about 1% and about 10%, about 5% and about 50%, about 5% and about 30%, about 5% and about 20%, about 10% and about 40%, about 10% and about 30%, about 20% and about 50%, about 20% and about 40%, about 20% and about 30%, or about 30% and about 40% by weight of the flavored product. In another example, carrier is added in an amount less than about 60%, about 50%, about 40%, about 30%, about 20%, about 10%, or about 5% by weight of the flavored product.

The amount of flavoring added may vary and generally depends on the nature of the flavor input. Some flavorings that are pure ingredients (such as menthol) or are already supplied in a carrier, such as PG and/or VG, may be introduced without the use of additional carrier, while others may require addition of carrier. The amount of carrier added may be between about 1% and about 50% by weight of the flavored product. While a greater weight percent may be used, as noted above, the final potency of the product should be considered because as more flavor/carrier is added, the potency of the finished concentrate will be reduced.

Various weight ratios of flavoring to carrier may be used. For example, the weight ratio of flavoring to carrier may be between 1:50 and 50:1, such as between about 1:50 and about 1:1, about 1:40 and about 1:1, about 1:30 and about 1:1, about 1:20 and about 1:1, about 1:10 and about 1:1, about 1:10 and about 1:2, about 1:10 and about 1:4, about 1:10 and about 1:6, about 1:8 and about 1:2, about 1:8 and about 1:4, about 1:6 and about 1:2, about 1:8 and about 1:2, about 2:1 and about 1:1, about 4:1 and about 1:1, about 8:1 and about 1:1, or about 12:1 and about 1:1. In any of the above or a further example, carrier and flavoring are added at a combined weight percent of the flavored product in an amount between about 1% and about 60%, about 1% and about 50%, about 1% and about 40%, about 1% and about 20%, about 1% and about 10%, about 10% and about 50%, about 10% and about 40%, about 10% and about 30%, about 10% and about 20%, about 20% and about 50%, about 20% and about 40%, about 20% and about 30%, about 30% and about 55%, about 30% and about 50%, about 30% and about 40%, about 40% and about 60%, or about 40% and about 50%. In another example, carrier and flavoring are added in a combined amount less than about 60%, 50%, 40%, 30%, 20%, 10%, or 5% by weight of the flavored product.

In one embodiment, the carrier is added in an amount between about 10% and about 45% by weight of the flavored product and the flavoring is added in an amount between about 3% and about 30% of the flavored product. The remaining portion of the flavored product may be provided by the extract.

In one embodiment, the carrier and flavoring are added in an amount between about 3% and about 30% by weight of the flavored product such that the flavored product provides a potency of 70% or greater when isolates and/or refined distillates are employed.

The flavoring may be mixed with the melted or softened resin within the carrier. The flavoring may be mixed with the carrier prior to addition and mixing with the resin. In some embodiments, the flavoring and carrier may be added separately. The flavor ingredients comprising or consisting of the flavoring and carrier may be provided in a solution or suspension. In one example, the flavor ingredients may be at room temperature or greater when added to the resin. For instance, the flavor ingredients may be added to the melt at about the same temperature as the resin, e.g., at about the working temperature of the resin.

The flavoring and carrier may be mixed with the resin to achieve dissolution. In one embodiment, the flavoring and carrier are mixed with the resin until a consistent viscosity is achieved. Mixing may be by hand, which may include stirring, or with the use of a mixer, homogenizer, or other suitable device to thoroughly mix the components into a homogenous mixture.

The flavor ingredients may typically be mixed with the melted or softened resin while the heat source continues to apply heat. The applied heat will typically be about the same or reduced with respect to the heat applied to melt or soften the resin. In another example, the melted or softened resin may be removed from the heat prior to addition of the flavoring or combination flavoring and carrier. In this example, the flavoring or combination flavoring and carrier should be mixed with the resin prior to recrystallization or substantial recrystallization or return to resinous form. If recrystallization or return to resinous form occurs during mixing, additional heat may be applied to allow complete dissolution of the flavoring of combination flavoring and carrier within the melt. Preheating the flavor ingredients prior to mixing with the melt may reduce opportunity for the resin to begin recrystallization or return to resinous form while mixing.

After mixing, the mixture may be allowed to cool. The resulting flavored concentrate may recrystallize completely or may exist as a resinous form. Cooling may typically be a room temperature. Temperatures above room temperature may slow cooling. In some embodiments, cooling may include subjecting the mixture to temperatures below room temperature. Cooling at temperatures below room may be used to generate different crystal sizes.

Following cooling, the product comprises a homogenous composition wherein the flavoring does not separate from the resinous product and is evenly distributed through the product.

The flavored products formulated as described herein may be consumed via existing methods of concentrate use—such as inhalation, which may be assisted by devices for dabs, shatter, budder, resin, waxes and related forms such as nails, e-nails, nectar collectors and related devices. Some embodiments may comprise or consist of addition of the flavored product directly or indirectly to foods, beverages, or smokable hemp products. For example, the flavored products may be used in cooking, baking, beverages such as smoothies, condiments etc. In a further example, flavored products, such as a flavored crumble, may be added to desserts, such as cakes or cookies, doughnuts, jellies or jams, or sweetened drinks. Coffee, mint, or methanol flavored dabs or crumble may be added to coffee, for example. Fruit flavored products, such as apple, apple cinnamon, banana, cranberry, peach, mango, grape, apricot, orange, lemon, currant, mangoes, peach, pear, pineapple, or pomegranate, may added to savory dishes such as chicken, beef, turkey, or pork. In one example, pineapple, mango, or other fruit flavored products may be added to a meat or vegetable stir fry. In another example, the flavored products may be combined with smokable hemp or *Cannabis* flower to add flavor and potency to the flower.

In one embodiment, a method of formulating a flavored bioactive extract includes heating the resin at a temperature between about 60° C. and about 95° C., preferably between 70° C. and about 95° C., or more preferably between 80° C. and about 93° C. until the extract melts or is suitably softened to form a workable extract melt. A combination flavoring and carrier may then be combined and mixed to dissolution with the extract melt. The flavoring and carrier may be combined in an amount between about 1% and about 60%, preferably between about 3% and about 50%, or more preferably between about 3% and about 30% by weight of the combined extract melt, flavoring, and carrier. The extract may comprise or consist of any suitable bioactive plant extract, such as any described herein (e.g., CBDa, THC Δ8, THC Δ9, THCa, CBG, CBN, CBC, CBDV and other cannabinoids, kavalactones, kratom, among others); any suitable flavoring, such as any flavoring described herein; and a non-lipophilic or hydrophilic flavor carrier, such as any carrier described herein in, e.g., PG, VG, or a mixture of VG and PG.

In one embodiment, a method of formulating a flavored bioactive extract includes heating the resin at a temperature between about 60° C. and about 100° C., preferably between 60° C. and about 90° C., or more preferably between 60° C. and about 85° C. until the extract melts or is suitably softened to form a workable extract melt. A combination flavoring and carrier is combined and mixed to dissolution with the extract melt. The flavoring and carrier may be combined in an amount between about 1% and about 50%, preferably between about 1% and about 40%, or more preferably between about 3% and about 20% by weight of the combined extract melt, flavoring, and carrier. The extract may comprise or consist of any suitable bioactive plant extract, such as any described herein (e.g., CBDa, THC Δ8, THC Δ9, THCa, CBG, CBN, CBC, CBDV and other cannabinoids, kavalactones, kratom, among others); any suitable flavoring, such as any flavoring described herein; and a hydrophilic flavor carrier, such as any carrier described herein in, e.g., PG, VG, or a mixture of VG and PG.

In one embodiment, a method of formulating a flavored bioactive extract includes heating the resin at a temperature about the melting temperature of the resin until the extract melts or is suitably softened to form a workable extract melt. A combination flavoring and carrier may then be combined and mixed to dissolution with the extract melt. The flavoring and carrier may be combined in an amount between about 1% and about 60%, preferably between about 3% and about 50%, or more preferably between about 3% and about 30% by weight of the combined extract melt, flavoring, and carrier. The extract may comprise or consist of any suitable bioactive plant extract, such as any described herein (e.g., CBDa, THC Δ8, THC Δ9, THCa, CBG, CBN, CBC, CBDV and other cannabinoids, kavalactones, kratom, among others); any suitable flavoring, such as any flavoring described herein; and a hydrophilic flavor carrier, such as any carrier described herein in, e.g., PG, VG, or a mixture of VG and PG. In another example, the heat is applied within about 10° C., about 5° C., about 4° C., about 3° C., about 2° C., or about 1° C. of the melting temperature of the resin. In a further example, the heat is applied at a temperature about 10° C., about 5° C., about 4° C., about 3° C., about 2° C., or about 1° C. above the melting temperature of the resin.

In one embodiment, a method of formulating a flavored bioactive extract includes heating the resin at about its melting temperature until the extract melts or is suitably softened to form a workable extract melt. A combination flavoring and carrier is combined and mixed to dissolution with the extract melt. The flavoring and carrier may be combined in an amount between about 1% and about 50%, preferably between about 1% and about 40%, or more preferably between about 3% and about 20% by weight of the combined extract melt, flavoring, and carrier. The extract may comprise or consist of any suitable bioactive plant extract, such as any described herein (e.g., CBDa, THC Δ8, THC Δ9, THCa, CBG, CBN, CBC, CBDV and other cannabinoids, kavalactones, kratom, among others); any suitable flavoring, such as any flavoring described herein; and a hydrophilic flavor carrier, such as any carrier described herein in, e.g., PG, VG, or a mixture of VG and PG. In another example, the heat is applied within about 10° C., about 5° C., about 4° C., about 3° C., about 2° C., or about 1° C. of the melting temperature of the resin. In a further example, the heat is applied at a temperature about 10° C., about 5° C., about 4° C., about 3° C., about 2° C., or about 1° C. above the melting temperature of the resin.

In a further example of any of the above embodiments, the flavor ingredients may comprise about 50%, about 40%, about 30%, about 20%, or about 10% or less flavoring, wherein the remainder comprises or consists of the carrier.

In various embodiments, the flavored product comprises an infused crumble formulated utilizing rapid crystallization rather than the heating step. For example, a method of formulating an uniformly flavor infused, e.g., homogeneously flavored, crumble may include combining a bioactive plant extract, flavoring, and carrier, as described herein, without application of heat above 60° C. Indeed, according to some embodiments, the methodology may be performed at room temperature. For example, the resin, flavoring, and carrier mixture may be homogenized to achieve complete dissolution of the ingredients. Example homogenization may include utilization of an overhead homogenizer. Homogenization time may vary, but about 15 minutes of mixing with an overhead homogenizer has been found to be sufficient in most formulations. Aqueous solution, e.g., water, such as distilled water, may then be added and the mixture may be further stirred to introduce the solution. The amount of solution is typically between about 50 mL and about 100 mL or less than about 100 mL per 400 mL of combined resin, flavoring, and carrier, although greater amounts may be used. The mixture may then be allowed to recrystallize for flavor infusion to take place. Recrystallization typically takes place in about 1 hr at around room temperature for a mixture under about 1 L. The resulting slurry may be subjected to one or more rounds of vacuum filtration and washing with distilled water and allowed to dry.

In some embodiments, the flavored product comprises an infused crumble formulated without utilizing heat or rapid crystallization. For example, a method of formulating a uniformly flavor infused, e.g., homogeneously flavored, crumble may include combining a bioactive plant extract, flavoring, and carrier, as described herein, without application of heat above 60° C. Indeed, in according to some embodiments, the methodology may be performed at room temperature. For example, the resin, flavoring, and carrier mixture may be homogenized to achieve complete dissolution of the ingredients. Example homogenization may include utilization of an overhead homogenizer. Homogenization time may vary, but about 15 minutes of mixing with an overhead homogenizer has been found to be sufficient in most formulations. The mixture is then sealed within a vessel and allowed to recrystallize for about 24 hours or longer. In some embodiments, longer periods such as days to weeks may be used, e.g., about 3 days, about 5 days, about 1 week, about 2 weeks, about 3 weeks, about 4 weeks, about 5 weeks, or greater. The mixture is preferably undisturbed during the recrystallization period. Thereafter, an aqueous solution, e.g., water, such as distilled water, may be added and briefly stirred. The amount of solution is typically between about 50 mL and about 100 mL or less than about 100 mL per 400 mL of combined resin, flavoring, and carrier, although greater amounts may be used. The resulting suspension of crystals may be separated from the bulk solution by vacuum filtrated to yields a crude flavored product. The crystals may then be washed with water or other suitable solution, typically at about room temperature or colder, to remove excess carrier solvent. The product may then be dried. For example, the product may be spread along a surface to air dry at about room temperature.

The flavored extracts may be crystalized or resinous concentrates such as badder, budder, sugar, sauce, or crystalline. Utilizing the methodologies described herein the flavored extracts have homogeneously flavored to provide a consistent flavor profile. The flavored products may retain substantially all the added flavoring. For example, dabs produced using direct heating of resin as described herein, retain all carrier components in the flavored product. eLiquid flavors may be particularly favorable flavorings for application in such a process since the flavored product may typically be consumed via vaporization. Unlike known flavored extracts, the flavor does not separate and is evenly distributed through the bulk. The flavored products may display refractive indices several thousandths lower than that of pure cannabinoid inputs in the molten state, which can be used to evaluate flavor uptake in the process.

The methodologies described herein may be utilized to create an environment that allows bioactive plant resin and flavor to combine while heated/dissolved and thereafter remain with the resin or carrier when cooled. In the case of pure inputs, such as menthol or menthol/PG/VG solutions, the resin and flavor combine via heat and/or dissolution. The environment is then altered via cooling or polarity increase that forces the resin and flavor to combine in a uniform fashion. As is apparent with crumble production, the introduced flavors will be incorporated into the crystalline product. Water washes may be utilized to remove excess carrier but bear little of the flavor introduced into the mix.

EXAMPLES

Example 1—Cookie Flavored CBD Product Using CBD Isolate, Cookie Flavoring Crystals/Powder, and VG Carrier For each 1 g of product, cannabidiol isolate (99%+pure), 500 mg, 1.59 mmol (50% w/w) is added to a 5 mL glass concentrate vessel and heat is applied by a heat source. In this example, the vessel is placed on a hot plate. The temperature is set to approximately 90° C. to promote a slow melting of the solid. Once melting is complete, Cookie Loops flavoring (Hertz and Selck 028.525, 90 mg, 9.015% w/w) in vegetable glycerin (410 mg, 40.985% w/w) is added to the melted concentrate and mixed thoroughly with stirring, by hand or mechanical to achieve a homogeneous mixture. The product is then removed from the heat and allowed to cool to room temperature to promote recrystallization/solidification of the cannabidiol-flavor/carrier mixture. Some additional stirring may be needed after crystallization/prior to use.

Example 2—Menthol Flavored CBD Production Using CBD Isolate, Menthol Flavoring Crystals/Powder, and VG/PG Carrier For each 1 g of product, cannabidiol isolate (99%+pure), 500 mg, 1.59 mmol (50% w/w) is added to a 5 mL glass concentrate vessel and heat is applied by a heat source. In this example, the vessel is placed on a hot plate. The temperature is set to about 90° C. to promote a slow melting of the solid. Once melting is complete, menthol (Mane T012489, 33.16 mg, 3.316% w/w) in vegetable glycerin (345.27 mg, 34.527% w/w) and propylene glycol (121.57 mg, 12.157% w/w) is added to the melted concentrate and mixed thoroughly with stirring, by hand or mechanical. The product is then removed from the heat and allowed to cool to room temperature to promote recrystallization/solidification of the cannabidiol-flavor/carrier mixture. Some additional stirring may be needed after crystallization/prior to use.

Example 3—Green Apple Dab 5 g of cannabidiol isolate powder (98%+purity) is placed in a glass vessel glass vessel and heat is applied by a heat source. In this example, the vessel is placed on a hot plate. The temperature is set to about 90° C. to promote a slow melting of the solid. Once melting is complete, 268 mg E_1853688 Sweet, 232 mg E_1853689 Fresh flavoring and 4.5 g VG is added to the melted concentrate and mixed thoroughly with stirring, by hand or mechanical. The product is then removed from the heat and allowed to cool to room temperature to promote recrystallization/solidification of the cannabidiol-flavor/carrier mixture. Some additional stirring of the green apple flavored dab may be needed after crystallization/prior to use.

Example 4—Coffee Dab Via VG 5 g of cannabidiol isolate powder (98%+purity) is placed in a glass vessel glass vessel and heat is applied by a heat source. In this example, the vessel is placed on a hot plate. The temperature is set to about 90° C. to promote a slow melting of the solid. Once melting is complete, 208 mg 7.80786 Coffee, 42 mg C104 Sugar booster (or equivalent) flavoring and 4.5 g VG is added to the melted concentrate and mixed thoroughly with stirring, by hand or mechanical. The product is then removed from the heat and allowed to cool to room temperature to promote recrystallization/solidification of the cannabidiol-flavor/carrier mixture. Some additional stirring of the coffee flavored dab may be needed after crystallization/prior to use.

Example 5—Coffee Dab Via VG and PG 5 g of cannabidiol isolate powder (98%+purity) is placed in a glass vessel glass vessel and heat is applied by a heat source. In this example, the vessel is placed on a hot plate. The temperature is set to about 90° C. to promote a slow melting of the solid. Once melting is complete, 208 mg 7.80786 Coffee, 42 mg C104 Sugar booster (or equivalent) flavoring, 3.5 g VG and 1.24 g PG is added to the melted concentrate and mixed thoroughly with stirring, by hand or mechanical. The product is then removed from the heat and allowed to cool to room temperature to promote recrystallization/solidification of the cannabidiol-flavor/carrier mixture. Some additional stirring of the coffee flavored dab may be needed after crystallization/prior to use.

Example 6—Mixed Berry Dab

For each 1 g of product, cannabidiol isolate (98%+pure), 500 mg, 1.59 mmol (50% w/w) is added to a 5 mL glass concentrate vessel and heat is applied by a heat source. In this example, the vessel is placed on a hot plate. The temperature is set to about 90° C. to promote a slow melting of the solid. Once melting is complete, 351 mg 029.180 Boysenberry and 149 mg NP5753 1% Raspberry ketone in PG (w/w) is added to the melted concentrate and mixed thoroughly with stirring, by hand or mechanical. The product is then removed from the heat and allowed to cool to room temperature to promote recrystallization/solidification of the cannabidiol-flavor/carrier mixture. Some additional stirring of the mixed berry flavored dab may be needed after crystallization/prior to use.

Example 7—Cool Melon Dab

For each 1 g of product, cannabidiol isolate (98%+pure), 500 mg, 1.59 mmol (50% w/w) is added to a 5 mL glass concentrate vessel and heat is applied by a heat source. In this example, the vessel is placed on a hot plate. The temperature is set to about 90° C. to promote a slow melting of the solid. Once melting is complete, 284 mg U_0026480 Watermelon, 114 mg 15_595 Honey melon, 43 mg E_1921202 Canteloupe and 59 mg Mentholated PG (10% w/w) is added to the melted concentrate and mixed thoroughly with stirring, by hand or mechanical. The product is then removed from the heat and allowed to cool to room temperature to promote recrystallization/solidification of the cannabidiol-flavor/carrier mixture. Some additional stirring of the cool melon flavored dab may be needed after crystallization/prior to use.

Example 8—Root Beer Dab

For each 1 g of root beer flavored dab, cannabidiol isolate (98%+pure), 750 mg (75% w/w) is added to a 5 mL glass concentrate vessel and heat is applied by a heat source. In this example, the vessel is placed on a hot plate. The temperature is set to about 90° C. to promote a slow melting of the solid. Once melting is complete, 250 mg U_0026501 Root Beer ART is added to the melted concentrate and mixed thoroughly with stirring, by hand or mechanical. The product is then removed from the heat and allowed to cool to room temperature to promote recrystallization/solidification of the cannabidiol-flavor/carrier mixture. Some additional stirring of the root beer flavored dab may be needed after crystallization/prior to use.

Example 9—Full Spectrum CBD Coffee Dab Via VG 5 g of full spectrum CBD distillate (amorphous crystals of 90%+purity) is placed in a glass vessel glass vessel and heat is applied by a heat source. In this example, the vessel is placed on a hot plate. The temperature is set to about 90° C. to promote a slow melting of the solid. Once melting is complete, 208 mg 7.80786 Coffee, 42 mg C104 Sugar booster (or equivalent) flavoring and 4.5 g VG is added to the melted concentrate and mixed thoroughly with stirring, by hand or mechanical. The product is then removed from the heat and allowed to cool to room temperature to promote recrystallization/solidification of the resin-flavor/carrier mixture. Some additional stirring of the coffee flavored dab may be needed after crystallization/prior to use.

Example 10—Green Apple Dab 5 g of cannabigerol (CBG) isolate powder (98%+purity) is placed in a glass vessel glass vessel and heat is applied by a heat source. In this example, the vessel is placed on a hot plate. The temperature is set to about 90° C. to promote a slow melting of the solid. Once melting is complete, 268 mg E_1853688 Sweet, 232 mg E_1853689 Fresh flavoring and 4.5 g VG is added to the melted concentrate and mixed thoroughly with stirring, by hand or mechanical. The product is then removed from the heat and allowed to cool to room temperature to promote recrystallization/solidification of the CBG-flavor/carrier mixture. Some additional stirring of the green apple flavored dab may be needed after crystallization/prior to use.

Example 11—Root Beer High THC Dab

For each 1 g of root beer flavored dab, full spectrum THC distillate oil (90%+pure), 750 mg (75% w/w) is added to a 5 mL glass concentrate vessel and heat is applied by a heat source. In this example, the vessel is placed on a hot plate. The temperature is set to about 90° C. to promote a workable consistency of the oil to approximately 200 cP viscosity. Once mixable, 250 mg U_0026501 Root Beer ART is added to the concentrate and mixed thoroughly with stirring, by hand or mechanical. The product is then removed from the heat and allowed to cool to room temperature to promote solidification of the cannabinoid-flavor/carrier mixture. Some additional stirring of the root beer flavored dab may be needed prior to use.

Example 12—Menthol Kavalactone Concentrate

For each 1 g of product, purified kavalactones extract (85% Kavain+pure), 500 mg, 1.59 mmol (50% w/w) is added to a 5 mL glass concentrate vessel and heat is applied by a heat source. In this example, the vessel is placed on a hot plate. The temperature is set to about 150° C. to promote a slow melting of the solid. Once melting is complete, menthol (Mane T012489, 33.16 mg, 3.316% w/w) in vegetable glycerin (345.27 mg, 34.527% w/w) and propylene glycol (121.57 mg, 12.157% w/w) is added to the melted concentrate and mixed thoroughly with stirring, by hand or mechanical. The product is then removed from the heat and allowed to cool to room temperature to promote recrystallization/solidification of the kavalactone-flavor/carrier mixture. Some additional stirring may be needed prior to use.

Example 13—Mango Lemonade Crumble

In a 1 L vessel, 21.84 g NPR0002 Orange lemonade, 11.82 g E_1863330 Lemon, 5 g U_0026571 Peach ART, 8.51 g C040 Green mango, 1.35 g E_1861152 Ripe and 1.77 g E_1861150 Juicy flavors are combined with 67 g of pure cannabidiol (CBD) isolate powder at about room temperature. A 50:50 PG/VG v/v solution (400 mL) is added to the flavoring and extract and the mixture is stirred with an overhead homogenizer for about 15 min or as otherwise required to ensure complete dissolution of the ingredients. When dissolution is complete, 200 mL of distilled water is added and the mixture is stirred for about 1 minute. The vessel is then removed from the homogenizer and allowed to sit at room temperature for 1 h, upon which recrystallization of the cannabidiol and flavor infusion takes place. The slurry is subject to vacuum filtration and washed twice with RT distilled water (2×300 mL) and air dried to afford mango lemonade crumble as a pale yellow powder.

Example 14—Berry Lemon Tart Crumble

In a 1 L vessel, 95 g 3209187441 Blueberry ART, 130 g E_18B6073 Lemon tart and 10 g NP5793RXR Butter key flavors are combined with 73 g of pure cannabidiol (CBD) isolate powder at about room temperature. A 50:50 PG/VG v/v solution (400 mL) is added to the flavoring and extract and the mixture is stirred with an overhead homogenizer for 15 min or as otherwise required to ensure complete dissolution of the ingredients. When dissolution is complete, 200 mL of distilled water is added and the mixture is stirred for 1 minute. The vessel is then removed from the homogenizer and allowed to sit at room temperature for 1 h, upon which recrystallization of the cannabidiol and flavor infusion takes place. The slurry is subject to vacuum filtration and washed twice with RT distilled water (2×300 mL) and air dried to afford berry lemon tart crumble as a pale yellow powder.

Example 15—Grape Lychee Lemonade Crumble

In a 1 L vessel, 20 g NPR0002 Orange lemonade and 10 g 026.803 Grape lychee flavors are combined with 75 g of pure cannabidiol (CBD) isolate powder at about room temperature. A 50:50 PG/VG v/v solution (400 mL) is added to the flavoring and extract and the mixture is stirred with an overhead homogenizer for 15 min to ensure complete dissolution of the ingredients. When dissolution is complete, 200 mL of distilled water is added and the mixture is stirred for 1 minute. The vessel is then removed from the homogenizer and allowed to sit at room temperature for 1 h, upon which recrystallization of the cannabidiol and flavor infusion takes place. The slurry is subject to vacuum filtration and washed twice with RT distilled water (2×300 mL) and air dried to afford grape lychee lemonade flavored crumble as a light orange powder.

Example 16—Watermelon Crumble

In a 1 L vessel, 57.5 g U_0026840 Watermelon flavor is combined with 75 g of pure cannabidiol (CBD) isolate powder at about room temperature. A 50:50 PG/VG v/v solution (400 mL) is added to the flavoring and extract and the mixture is stirred with an overhead homogenizer for 15 min to ensure complete dissolution of the ingredients. When dissolution is complete, 200 mL of distilled water is added and the mixture is stirred for 1 minute. The vessel is then removed from the homogenizer and allowed to sit at room temperature for 1 h, upon which recrystallization of the cannabidiol and flavor infusion takes place. The slurry is subject to vacuum filtration and washed twice with RT distilled water (2×300 mL) and air dried to afford watermelon flavored crumble as an off-white to pale yellow powder.

Example 17—Watermelon Crumble

In a 1 L vessel, 57.5 g U_0026840 Watermelon flavor is combined with 75 g of pure cannabinol (CBN) isolate powder at about room temperature. A 50:50 PG/VG v/v solution (400 mL) is added to the flavoring and extract and the mixture is stirred with an overhead homogenizer for 15 min to ensure complete dissolution of the ingredients. When dissolution is complete, 200 mL of distilled water is added and the mixture is stirred for 1 minute. The vessel is then removed from the homogenizer and allowed to sit at room temperature for 1 h, upon which recrystallization of the cannabinol and flavor infusion takes place. The slurry is subject to vacuum filtration and washed twice with RT distilled water (2×300 mL) and air dried to afford watermelon flavored crumble.

Example 18—Melon Berry Crumble

In a 1 L vessel, 16.01 g (1.60% w/w) MANE U_0026830 Strawberry, 20.21 g (2.02% w/w) MANE U_0026840 Watermelon and 31.42 g (3.14% w/w) MANE U_0026827 Sweet Strawberry are combined with 74.3 g of pure cannabidiol (CBD) isolate (98%+purity) at about room temperature. A 50:50 PG/VG v/v solution (400 mL) is added to the flavoring and extract and the mixture is stirred with an overhead homogenizer for about 15 min or as otherwise required to ensure complete dissolution of the ingredients. When dissolution is complete, 200 mL of distilled water is added and the mixture is stirred for about 1 minute. The vessel is then removed from the homogenizer and allowed to sit at room temperature for about 1 h, upon which recrystallization of the cannabidiol and flavor infusion takes place. The slurry is subject to vacuum filtration and washed twice with RT distilled water (2×300 mL) and air dried to afford melon berry crumble (96.83 g) as an off-white powder with 74.8% CBD potency.

Example 19—Melon Berry Crumble.

In a 1 L vessel, 16.01 g (1.60% w/w) MANE U_0026830 Strawberry, 20.21 g (2.02% w/w) MANE U_0026840 Watermelon and 31.42 g (3.14% w/w) MANE U_0026827 Sweet Strawberry are combined with 74.3 g of pure cannabidiol (CBD) isolate (98%+purity)) at about room temperature. A 50:50 PG/VG v/v solution (400 mL) is added to the flavoring and extract and the mixture is stirred with an overhead homogenizer for 15 min to ensure complete dissolution of the ingredients. The vessel is sealed and allowed to sit undisturbed for recrystallization and flavor infusion to take place. This can occur as soon as 24 h but can be allowed to extend for longer periods (multiple days to weeks), so long as the container is sealed. Once crystallization is complete, 200 mL of distilled water is added and the mixture is briefly stirred by hand and the suspension of crystals is separated from the bulk solution by vacuum filtration to yield the crude flavored product. These crystals are then washed with room temperature or cold water to remove excess carrier solvent. The product is collected and spread out to air dry at room temperature to afford the dry flavored crumble in 94% CBD potency by HPLC.

The methodologies presented above extend to preparation of other flavored concentrate products such as those based on CBDa, THC (Δ8 and Δ9), THCa, CBG, CBN, CBC, CBDV and other cannabinoids, kavalactones, kratom (mitragynine and 7-hydroxymitragynine, among others) preparations and formulated mixtures of any of the above. According to the teachings herein, those having skill in the art may apply the methodologies to additional plant extracts to integreate or infuse such lipophilic extracts with non-lipophilic flavorings. The above examples may also be scaled to achieve desired weight of final products.

This processes described herein for flavor introduction into lipophilic bioactive plant extracts is unique in that it allows for non-lipophilic flavorings to be incorporated into a stable, finished final product that meets the consistency and texture needs of the consumers, allowing them to use the product interchangeably in devices intended for *Cannabis* concentrate consumption. The hydrophilic flavor carrier, such as PG, VG or a combination of both, when introduced in a low heat process or in the appropriate stoichiometry to the resin, creates an environment that allows flavors to be introduced into the extract, e.g., cannabinoid extract, upon cooling (dabs) or increasing the hydrophilic nature of the solution (crumble). The flavorings or mixtures of flavorings that may be used according to the present description may be complex with dozens of active flavor ingredients (AFIs), that if introduced in pure form directly into the plant resins, such as cannabinoid resins, would simply dissolve the resin—rendering it unworkable, or separate from the solid providing a mixture that is not uniformly flavored. Current methods of introducing lipophilic flavors such as terpenes into a resin rely on the high efficacy of such inputs in very small amounts, lowering the resin's viscosity but still allowing it to we workable and consumable. The method described herein represents to our knowledge the first general process for introduction of previously incompatible flavors into lipophilic cannabinoid matrices, whether or not the carriers are removed from the system in further processing or used directly.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and all intervening ranges and percentages, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" or "about" are intended to include +/−10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. A method of formulating a homogeneous flavored bioactive plant product, the method comprising:
    applying heat to a bioactive plant extract until the extract is melted or softened to a workable consistency to form a melt, wherein the bioactive plant extract is lipophilic;
    combining a non-lipophilic or hydrophilic flavoring and non-lipophilic or hydrophilic flavoring carrier with the melt until dissolution of the flavoring and flavoring carrier in the melt; and
    cooling the melt mixture of flavoring, flavoring carrier, and extract,
    wherein the bioactive plant extract comprises a cannabinoid, cannabinoid acidic precursor, kavalactone, flavonoid, alkaloid, or combination thereof,
    wherein at room temperature the flavoring is evenly distributed and does not separate from the bioactive plant extract to provide a flavored bioactive plant product that is crystallized or resinous.

2. The method of claim 1, wherein the heat is applied between about 75° C. and about 100° C.

3. The method of claim 1, wherein the heat is applied at a temperature within about 30° C. of the melting point of the bioactive plant extract.

4. The method of claim 1, wherein the heat is applied at a temperature within about 10° C. of the melting point of the bioactive plant extract.

5. The method of claim 1, wherein the bioactive plant extract comprises a crystalline/resinous lipophilic plant extract.

6. The method of claim 1, wherein the bioactive plant extract comprises the cannabinoid or cannabinoid acidic precursor.

7. The method of claim 6, wherein the cannabinoid or cannabinoid acid precursor is selected from one or more of cannabidiol (CBD), CBDa, cannabigerol (CBG), cannabinol (CBN), tetrahydrocannabinol (THC) Δ8 or Δ9, THCa, cannabichromene (CBC), or cannabidivarin (CBDV).

8. The method of claim 1, wherein the flavoring carrier comprises a GRAS for inhalation carrier.

9. The method of claim 1, wherein the flavoring carrier comprises of vegetable glycerin VG, propylene glycol PG, or combination thereof.

10. The method of claim 1, wherein the flavoring comprises a menthol or coffee flavoring.

11. The method of claim 1, wherein the flavoring and flavoring carrier are combined in an amount about 30% or less of the flavored bioactive plant product.

12. The method of claim 1, wherein the bioactive plant extract comprises the kavalactone extract and the heat is applied at a temperature between 140° C. and 160° C.

13. The method of claim 7, wherein the heat is applied at a temperature between about 60° C. and about 95° C.

14. The method of claim 13, wherein the heat is applied at a temperature between about 80° C. and about 95° C.

15. The method of claim 1, wherein the flavored bioactive plant product is resinous.

16. The method of claim 15, wherein the flavoring is combined in an amount between 10% and 25% by weight of the flavored bioactive plant product.

17. The method of claim 1, wherein the flavored bioactive plant product is crystallized.

18. The method of claim 1, wherein upon cooling the bioactive plant extract is infused with the flavoring.

19. The method of claim 18, wherein the flavored bioactive plant product does not include solvents.

20. The method of claim 1, wherein the bioactive plant extract comprises an extract of a plant in genus *Cannabis*.

21. The method of claim 1, wherein the bioactive plant extract comprises the alkaloid.

22. The method of claim 21, wherein the alkaloid is selected from one or more true alkaloids, protoalkaloids, pseudoalkaloids, or combination thereof.

23. The method of claim 21, wherein the alkaloid comprises caffeine, psylocin/psilocybin, mitragynine, 7-OH-mitragynine, yohimbine, voacangine, or combination thereof.

24. The method of claim 21, wherein the bioactive plant extract comprises an extract of kratom and includes the alkaloids mitragynine and 7-OH-mitragynine.

25. The method of claim 1, wherein the bioactive plant extract is an extract isolate or distillate.

26. The method of claim 1, wherein the bioactive plant extract comprises a crude, refined, purified, or combinational extract.

27. The method of claim 1, wherein the bioactive plant extract is a partial, full, or broad spectrum extract.

* * * * *